United States Patent [19]

Mayoral

[11] 4,447,226
[45] May 8, 1984

[54] SURGICAL ASPIRATOR VALVE APPARATUS

[76] Inventor: Armando G. Mayoral, Av. Ruiz No. 558, Ensenada, Mexico

[21] Appl. No.: 355,457

[22] Filed: Mar. 8, 1982

[30] Foreign Application Priority Data

Oct. 18, 1981 [MX] Mexico .................................. 189850

[51] Int. Cl.³ .............................................. A61M 1/00
[52] U.S. Cl. ........................................ 604/73; 604/31; 604/32; 604/119
[58] Field of Search ................. 604/27, 28, 30, 31, 604/33, 32, 35, 45, 50, 65, 73, 118, 119, 120, 604/129, 131–141, 151–153, 147, 149, 245, 248, 604/313–315, 4, 121

[56] References Cited

U.S. PATENT DOCUMENTS

| | | | |
|---|---|---|---|
| 3,048,192 | 8/1962 | Murphy, Jr. | 604/32 X |
| 3,429,313 | 2/1969 | Romanelli | 604/31 |
| 3,930,505 | 1/1976 | Wallach | 604/28 X |
| 3,955,574 | 5/1976 | Rubinstein | 604/120 |
| 4,193,406 | 3/1980 | Jinotti | 604/33 X |
| 4,315,506 | 2/1982 | Kayser et al. | 604/28 |
| 4,327,724 | 5/1982 | Birk et al. | 604/121 X |
| 4,395,258 | 7/1983 | Wang et al. | 604/65 |

Primary Examiner—C. Fred Rosenbaum
Assistant Examiner—Michelle N. Lester
Attorney, Agent, or Firm—Harlan P. Huebner

[57] ABSTRACT

A medical aspirator including an automatic valve means to reverse the flow of air upon stoppage of the suction system whereby the stoppage may be dislodged and the normal suction function of the aspirator is reinstituted. The aspirator includes a spring loaded suction responsive trigger means to rotate the valve means.

7 Claims, 6 Drawing Figures

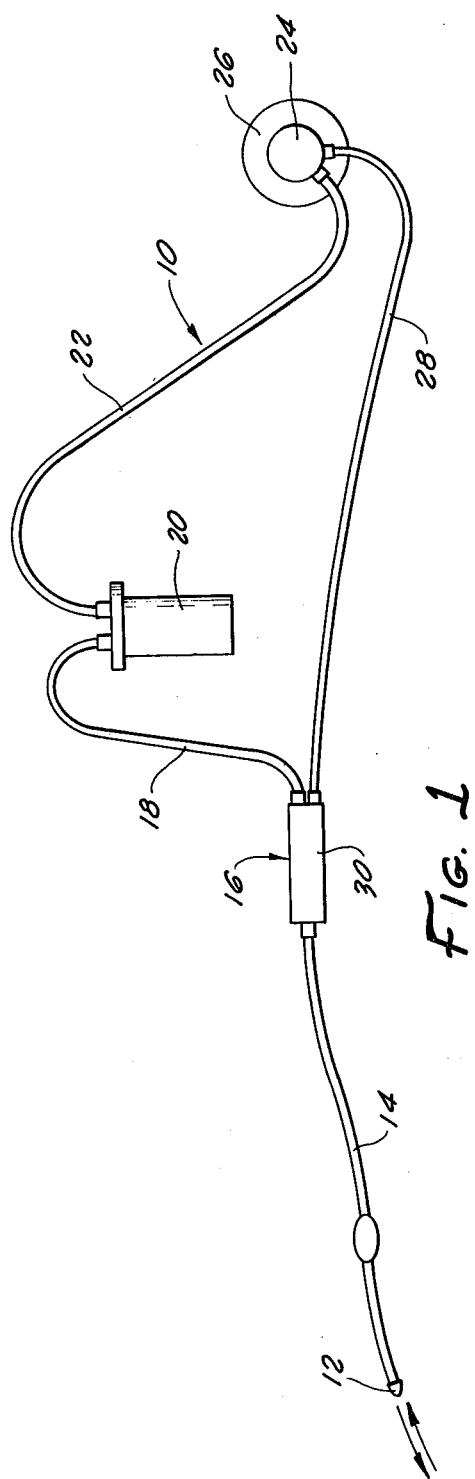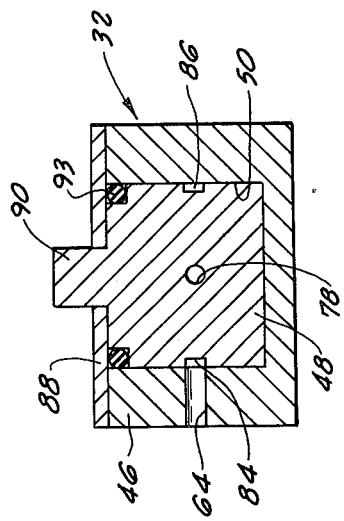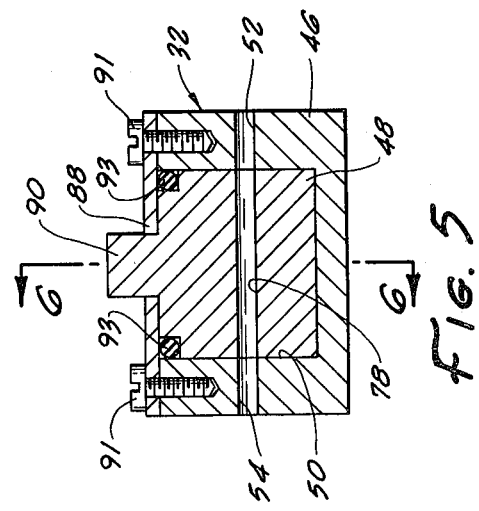

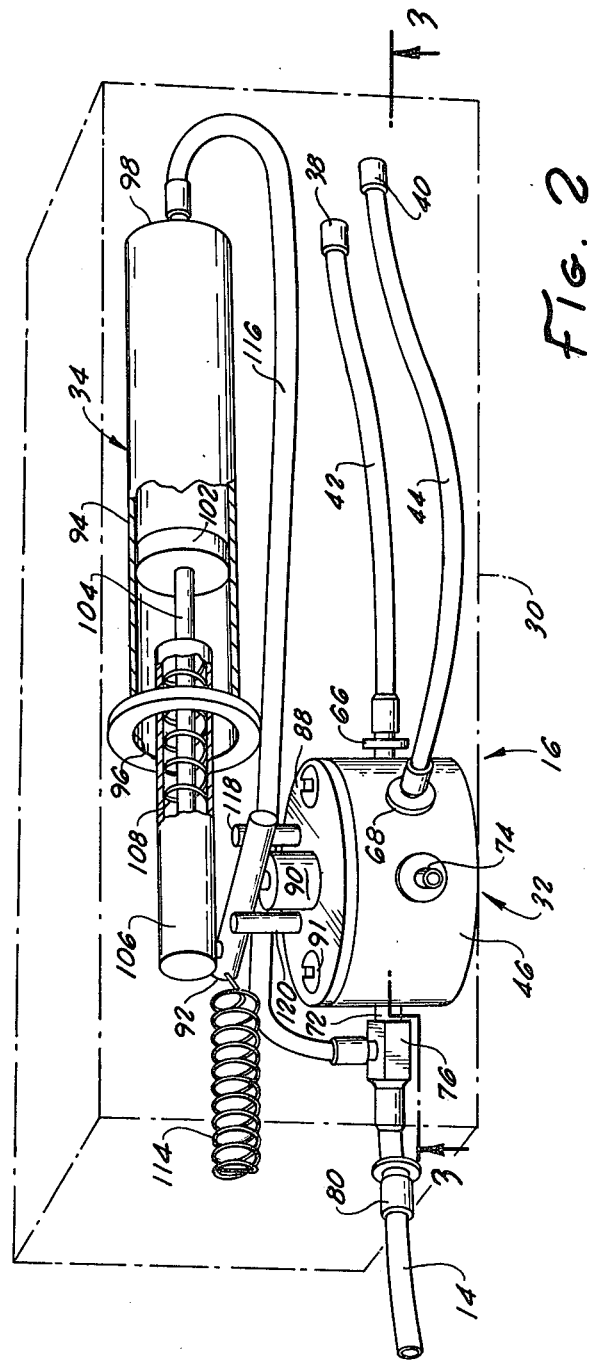

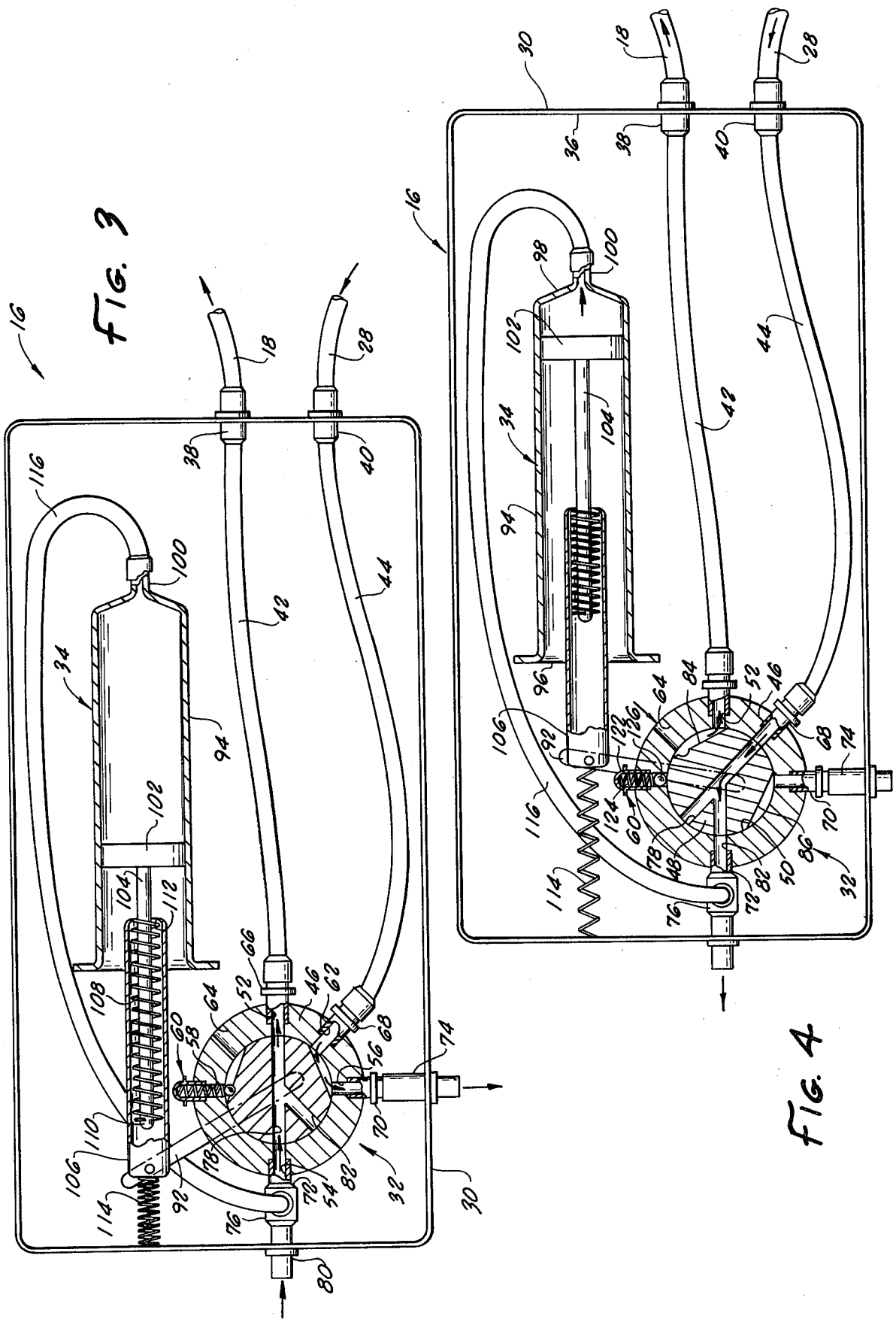

SURGICAL ASPIRATOR VALVE APPARATUS

BACKGROUND OF THE INVENTION

Medical and surgical aspirators have been known for some time. The purpose of the aspirator is to remove blood, fluid and other foreign material from an incision or wound. The aspirator is in effect a suction pump which will draw the material through a tube to a deposit container.

The normal aspirator can be either left in the wound or opening in the body during an operation or it may be moved manually in and out of the wound by the hand of either the doctor or surgical nurse in attendance.

With the present state of art of aspirators should any of the blood clots or any other materials be larger than the conventional nozzle on the aspirator that material will be held to the nozzle by the suction. This will of course stop the suction of material and render the aspirator useless until it is removed. The only known way which the offending large material maybe removed is either when the surgeon takes his hand and physically crushes it or condenses it or removes it so that the aspirator is free to continue with its suction. The other way is for the physican to merely try to shake the end of the aspirator so that the unwanted material is removed in this fashion.

Both of the above presently known methods of removal of the stoppage material is time consuming which in the case of delicate surgery can be very vital to the surgeon performing the surgery. It also in some instances requires the surgeon to remove his hand from the scalpel or other implements that he is using in order to physically remove the unwanted material. This again has caused considerable loss of time and could possibly endanger the life of the patient.

SUMMARY OF THE INVENTION

It is a primary purpose of this invention to utilize an automatic valve means in a surgical aspirator system which can close and open depending upon whether or not the opening of the aspirator is open or closed by a stoppage of material.

The valve means forming the primary part of the invention is normally positioned in an open position whereby there is a constant draw of suction through the valve when it is operating properly. Upon closure of the suction line because of an enlarged blood clot or other foreign matter which cannot pass through the nozzle the valve means will automatically close the suction line. This will in turn reverse the air flow and allow air to pass through the valve in the opposite direction from the suction and in the same line to blow the object off of the nozzle without the need of hands or time spent in the surgery to physically remove the material.

Another object of this invention is to provide an automatic valve means in the line of an aspirator which includes biasing means such as springs in order to return the valve from its closed blowing position to its generally open position.

Another object of the invention is to provide a rotatable, valve means including various fittings, and passages which can cause the diversion of the suction and replace it with a blowing of air.

It is still another object of the invention to provide an aspirator automatic valve mechanism which is compact and economical to a manufacturer and install in existing systems.

Further objects and advantageous of the invention may be brought out in the following part of the specification wherein small details have been described for the competence of disclosure, without intending to limit the scope of the invention which is set forth in the appended claims.

BRIEF DESCRIPTION OF THE DRAWINGS

These advantageous may be more clearly understood from the following detailed description and in by reference to the drawings in which:

FIG. 1 is a view of a surgical respirator system embodying the automatic valve mechanism;

FIG. 2 is a perspective view of the automatic valve mechanism of the surgical aspirator;

FIG. 3 is a partial cross sectional view taken on line 3—3 of FIG. 2 showing an automatic valve mechanism in open suction position;

FIG. 4 is a view similar to FIG. 3 of the automatic valve mechanism of the surgical aspirator but with the valve in the closed position where the suction line is closed and a reverse flow of air is being passed from the valve;

FIG. 5 is a cross sectional view of the valve per se as illustrated in FIGS. 2, 3 and 4; and FIG. 6 is a cross sectional view of the valve of FIG. 5 taken on line 6—6 of FIG. 5.

DETAILED DESCRIPTION OF THE PREFERRED EMBODIMENT

Turning now to the drawings and particularly FIG. 1 there is illustrated therein an aspirator system generally designated 10 which is primarily used in surgery. The system 10 includes an aspirator nozzle 12 secured to suction line 14 which extends to and is secured to an automatic valve mechanism generally designated 16.

From the automatic valve mechanism 16 a second suction line 18 extends to a receptacle 20 and extending from the receptacle 20 is a further suction line 22 which passes through a conventional suction pump 24 connected to a motor such as 26.

From the suction pump 24 there is an air line or air conduit 28 which extends to the automatic valve mechanism 16.

In operation the aspirator system 10 operates by turning on the motor 26 which in turn will turn on the suction pump 24. When the suction pump 24 is in operation, air will be drawn through the nozzle 12 such as seen by the arrow through the suction line 14 into the automatic valve mechanism 16 through the second suction line 18 and anything that has been drawn through the line to this point will then be deposited into the receptacle 20. The suction again is created in the container which will remove the air through suction line 22 back to the suction pump 24. The air line 28 will in turn blow air forwardly to the automatic valve mechanism and in normal position the air from that line 28 will be bleed from the automatic valve mechanism 16 to the atmosphere.

However, should an obstruction occur at the nozzle 12 the automatic valve mechanism 16, to be described in further detail, will in effect close the suction line 14 so that air in the air line 28 instead of being bleed to the atmosphere through the mechanism will be forced through various ports and to the suction line 14 outwardly through the nozzle 12 as shown in the direction of the arrow. As the air flow reverses and moves outwardly through the nozzle any or foreign material which is to large to actually go through the nozzle of the aspirator system 10 will be blown outward and discharged from the nozzle.

In this way it can be seen that the surgeon during the operation confronted with the blockage at the nozzle 12 has merely to remove the nozzle and place it over a receptacle near the place of operation. The automatic valve mechanism 16 will force the obstruction from the nozzle 12 into the receptacle and then when it is removed to automatically reinstate the suction process whereby blood and other material may be removed from the wound.

Turning now to the automatic valve system 16 illustrated in FIGS. 2, 3 and 4 there is a housing 30 within which is mounted an automatic valve means 32 and spring loaded suction responsive trigger means generally designated 34. The housing 30 on end wall 36 is fitted with a pair of couplings 38 and 40 which extends through the wall 36 as best seen in FIGS. 3 and 4. These couplings are adapted to receive and retain on the exterior of the housing 30, the suction line 18 and the air line 28. Connected to the couplings 38 and 40 are interior suction line 42 and interior air line 44. The suction line 42 and air line 44 extends inwardly within the housing 30 to the valve means 32.

The valve means 32 preferably includes an exterior cylindrical stationary portion 46 which may be mounted by any convenient means to the housing 30. The valve portion or interior rotatable valve section 48 is also cylindrical and fits snuggly within the interior annular surface 50 of the exterior cylindrical stationary portion 46. The interior rotatable valve section 48 is adapted to rotate within the exterior stationary portion 46.

The exterior cylindrical stationary portion 46 includes six bores extending therethrough. There is a rear bore 52 and diametrically opposite a front bore 54 and at 90° thereto an air outlet bore 56 and diametrically opposite thereto a bore 58 which receives locking means 60. In addition there is spaced between bores 52 and 56 an air inlet bore 62 and spaced between bore 52 and 58 is an air intake bore 64.

Each of these bores with the exception of bore 58 and 64 are fitted with couplings 66, 68, 70 and 72 respectively. These are similar in nature to couplings 38 and 40. The interior suction hose 42, as can best be seen in FIGS. 3 and 4, is connected to the coupling 66 adjacent exterior cylindrical stationary portion 46 of the valve 32. With regard to the interior air hose 44 it in turn is connected to the coupling 68 of the exterior cylindrical stationary portion 46 of the valve 32.

The coupling 70 is in turn connected to the short air bleeder hose 74 which preferably extends through the housing 30, as best seen in FIGS. 3 and 4.

At the front of the valve 32 the coupling 72 is mounted into the stationary portion 46 and extends outwardly to a point where a T coupling 76 is connected thereto.

With regard to the interior rotatable valve section 48, extending axially therethrough is an air suction bore 78. This bore as can be seen in FIG. 3 is normally in direct alignment and communication with the couplings 66 and 72 and when in the position shown in FIG. 3 will create a complete passage way from the suction line 14 which is connected to coupling 80 through interior line 18 and 42 to the receptacle 20 and then through line 22 to the suction pump 24. Angled at approximately 45° to the plane of the bore 78 is an air diversion bore 82. This bore 82 communicates with bore 78 as can be seen in both FIGS. 3 and 4.

In addition to the bores aforementioned the interior rotatable valve section 48 includes a flattened cord section 84 and opposite thereto a second flattened cord section 86. These cord sections 84 and 86 are actually cut away from the cylindrical valve section 48 leaving a space between the valve section 48 and the interior surface 50 of the fixed or stationary portion 46.

In order to complete the assembly of the valve means 32 there is provided a cover 88 which is mounted over both the exterior and interior portion 46 and 48 and is secured to the exterior fixed portion 46 by means of screw 91. There is also provided an O ring 93 as best seen in FIGS. 5 and 6 to complete the valve seal when the interior valve section 48 rotates within the exterior stationary portion 46. Projecting from the valve section 48 is a stub staft 90. A rocker or pivot arm 92 is connected to the shaft 90 and extends outwardly and at its other end is connected to the spring loaded suction responsive trigger means 34.

This trigger means 34 includes an elongated cylinder 94 having an open end 96 and an opposite closed end 98. Extending from the closed end 98 is a reduced neck portion 100 which communicates with the interior of the elongated cylinder 98. Mounted within the elongated cylinder 94 is a piston 102 which includes a piston rod 104 extending from the piston 102 into a tubular spring housing 106. Within the housing 106 a compression spring 108 is connected to the end 110 of the piston rod 104 and the other end thereof is biased against the front wall 112. The elongated spring housing 106 is pivotedly connected to the rocker arm 92.

In addition there is provided a tension spring 114 which extends from the rocker arm 92 to the housing 30 where it is connected thereto. To complete the assembly of the trigger means 34 there is a secondary suction line 116 which extends from the reduced neck portion 100 to the T coupling 76.

In operation the aspirator system when turned on will create a direct line of suction through the nozzle 12 the valve 32 to the receptacle 20 and then back to the suction pump 24. In order to maintain the proper alignment wherein the inner valve section 48 is in the open suction position such as shown in FIG. 3 the resilient spring 114 will bias the rocker arm 92 forwardly as seen in FIG. 3 so that the bore 78 is in direct alignment with the coupling 72 and 66. In this particular positioning air will be sucked as shown by the arrows in FIG. 3 through the nozzle 12 the hose 14, coupling 80, the interior suction hose 42 and suction hose 18. On the return the air from the suction pump 24 will be pumped out through the air hose 28 and then to the interior airhose 44 through the coupling 68 and because of the arrangement of the interior section 48 through the flattened space created by the flattened cord section 86 and them directed through the bore 56 and coupling 70 and air bleeder hose 74 to the atmosphere.

As thus can be seen, this continual cycle of sucking the air through the hose 14 and bleeding the same through the air bleeder hose 74 will be maintained and will allow blood and other material within a wound or during an operation to be removed by the surgical team. However, upon the blockage of the nozzle 12 by a piece of material which is substantially larger than the nozzle opening 12 the suction which has heretofore been described will immediately be reduced or cut off in the hose 14 and through coupling 80. At this point, as can best be seen from FIG. 4, suction will be created on the trigger responsive means 34 by drawing air through the elongated cylinder 94 and hose 116 through the T coupling 76 and thence through the interior air suction hose 42. This particular movement or suction generally being momentary is sufficient to draw the piston 102, the piston rod 104 and the housing 106 forwardly toward the end 98 of the elongated cylinder 94. In this way the rocker arm 92 is pivoted forwardly which in turn will rotate the interior rotatable valve section 48 to the air intake position shown in FIG. 4. There is also provided on top cover 88 a pair of stop bars 118 and 120 which will prevent the rocker arm from moving beyond the appropriate alignment either for that shown in FIG. 3 or 4.

When the valve is in the air intake position, as shown in FIG. 4, created by movement of the piston 102 it can be seen that the suction flow from nozzle 12 and line 14 through the valve is curtailed and completely stopped. In order not to freeze up the suction line air is drawn in through the bore 64, and through the area created by the flattened cord section 84. This will allow the air to be drawn in through the bore 64 and through the bore 52, coupling 66 and through the interior suction hose 42 completing the circuit as previously described. In the meantime the air however which is being forced through the line 44 toward the valve and which normally is bled off through the bleeder hose 74 is now channeled through a portion of the air intake bore 78 and then through the air diverging bore 82 through the hose 14 to the nozzle 12 which in turn will dislodge by air pressure any foreign matter that has been wedged to the nozzle during the operation. In this way it can be seen that the surgeon's additional hand is not necessary to remove the blood clot or other material which is to large to pass through the nozzle but it may be instantaneously blown off of the suction nozzle 12 into a receptacle.

As soon as the obstruction is removed from the nozzle 12 then the pressure extending through hose 116 is increased and the valve will return by the aid of the tension spring 114 to its normally open suction position as seen in FIG. 3.

In order to prevent the rotatable valve section 48 from moving to freely within the exterior portion there is provided a spring loaded locking means 60 which includes a cap 122 secured in the bore 58. Within the cap 122 there is a spring 124 which includes a ball 126. It should be noted that the cord surface 84 of the inner section 48 is formed with a depression or seat so that it may receive the ball which is always urged downwardly by the spring. In this way it can be assured that the valve 32 will normally remain in its open position until such time as the change in pressure and suction will overcome the ball and rotate the inner valve section 48 to that position as shown in FIG. 4.

Thus as can be seen that the automatic valve mechanism is such that it could be constantly rotating dislodging blood clots and other matter larger than the nozzle very quickly and wih great ripidity during the course of an operation or surgery upon a patient.

It should also be appreciated that any of the majority of the parts of this invention can be formed from plastic or metal but that the type of material utilized in the invention herein described is immaterial and does not play an active part in the invention thereof.

The invention and its attendant advantages will be understood from the foregoing description and it will be apparent that various changes may be made in the form and method of making, construction and arrangements of the parts without departing from the spirit and scope thereof or sacrificing its material advantages, the arrangements herein before described being merely by way of example. I do not wish to be restricted to the specifid form, method, or uses mentioned, except as defined in the accompanying claims, wherein various portions have been separated for clarity of reading and not for emphasis.

I claim:

1. A non-cyclical medical aspirator system adapted to automatically remove large particles of matter and prevent clogging of said system including a nozzle connected to an air suction line which line moves to a vacuum waste receptacle and continues to a suction pump having motive means to activate said pump, and an air line leading from said pump to discharge air drawn through said pump wherein said system includes:
    a housing interposed within said suction line between said nozzle and said waste receptacle;
    a single automatic non-cyclical valve means mounted in said housing including a valve having air suction and discharge bores and a rotatable portion, said valve connected to said suction line and said air line which valve is normally in an open suction position; and
    a pressure responsive means connected to said rotatable portion of said valve, whereby when the suction pressure is reduced caused by a blockage of said system said means will automatically move and rotate said rotatable portion and thus reverse the normal suction flow of air to discharge air therefrom through said nozzle to remove said large particles of matter.

2. A medical aspirator system as defined in claim 1 where said automatic non-cyclical single valve includes:
    an exterior fixable portion including a cylindrical inner wall and said rotatable portion is a cylindrical inner portion mounted in said fixable portion;
    a pair of generally opposed bores extending through the fixable portion;
    a suction bore extending through said rotatable portion for creating an air suction passage through said valve; and
    an air discharge bore in said rotatable portion angled relative to said air suction bore and intersecting said suction bore for creating an air discharge passage when aligned with one of said generally opposed bores.

3. A medical aspirator system as defined in claim 1 wherein said pressure responsive means connected to said rotatable portion includes:
    a cylinder connected to said housing;
    a plunger means slidably mounted in said cylinder;
    a rocker arm interconnecting said plunger means and said rotatable portion of said valve; and
    a pressure responsive means suction line from said cylinder to said air suction line of said system which when said aspirator system is blocked will divert suction in said pressure responsive means suction line reducing pressure in said cylinder causing said plunger to slide and rotate said valve to reverse the flow of air and discharge the same through said nozzle.

4. A medical aspirator as defined in claim 3 wherein there is included:
- a resistance spring secured to said rocker arm to normally maintain said automatic non-cyclical single valve in said open suction position which is yieldable by suction in said pressure responsive means to rotate said valve to reverse the air flow and discharge the same through said nozzle.

5. A non-cyclical aspirator system for use in surgery adapted to automatically remove large particles of matter and prevent clogging of said system, comprising:
- a nozzle for engaging blood clots and other matter;
- a first air suction line connected to said nozzle and extending to a waste receptacle;
- a suction pump with means to activate the same;
- a second air suction line extending from said receptacle to said pump;
- a return air discharge line extending from said pump;
- a single automatic non-cyclical valve means interposed in said first suction line and connected to said air line normally biased in an open suction position whereby said blood clots and other matter may be sucked through said nozzle, said first suction line and said valve to said receptacle, yet yieldable upon pressure change to move to an air intake position wherein said air flow is reversed and air will pass from said return air line through said valve, said first suction line and out said nozzle to discharge said large particles of matter.

6. An aspirator system as defined in claim 5 wherein said single automatic non-cyclical valve means includes:
- a pressure responsive means coupled to said valve to move said valve between said open suction position and said air intake position.

7. An aspirator system as defined in claim 6 wherein said pressure responsive means includes:
- a secondary suction line connected to said first air suction line;
- a cylinder open at one end and having a restrictive opening at said other end;
- said secondary suction line connected to said restrictive opening;
- a plunger slidably mounted in said cylinder and united with said valve whereby a change of pressure in said first air suction line will cause air suction to be applied in secondary suction hose whereby said plunger is drawn forward and in turn it moves said valve from said open suction position or said air intake position.

* * * * *